United States Patent [19]

Vandenburgh

[11] Patent Number: 5,153,136
[45] Date of Patent: Oct. 6, 1992

[54] APPARATUS FOR GROWING TISSUE SPECIMENS IN VITRO

[76] Inventor: Herman H. Vandenburgh, 22 Chapin Rd., Barrington, R.I. 02806

[21] Appl. No.: 472,347

[22] Filed: Jan. 30, 1990

Related U.S. Application Data

[62] Division of Ser. No. 223,292, Jul. 22, 1988, Pat. No. 4,940,853.

[51] Int. Cl.⁵ .............................................. C12M 3/00
[52] U.S. Cl. .................................. 435/284; 435/289; 435/316
[58] Field of Search ................. 435/1, 240.23, 240.241, 435/240.243, 284–286, 287, 289, 299–301, 316, 809, 3; 73/794, 806, 811

[56] References Cited

U.S. PATENT DOCUMENTS

| | | | |
|---|---|---|---|
| 4,762,794 | 8/1988 | Nees | 435/284 |
| 4,822,741 | 4/1989 | Banes | 435/301 |
| 4,851,354 | 7/1989 | Winston et al. | 435/284 |

OTHER PUBLICATIONS

Bray, "Axonal Growth in Response to Experimentally Applied Mechanical Tension", Developmental Biology, vol. 102 (1984) pp. 379–389.
Buck, "Reorientation Response of Cells to Repeated Stretch and Recoil of the Substratum", Exp. Cell Res., vol. 127 (1980), pp. 470–474.
Klein–Nulend, "Influence of Intermittent Compressive Force . . . ", The Journal of Biological Chemistry, vol. 232, No. 32, (1987), pp. 15490–15495.
Lanyon et al., "Static VS. Dynamic Loads As An Influence On Bone Remodelling", Journal of Biomechanics, vol. 17, No. 12 (1984), pp. 897–905.
Leung et al., "A New In vitro System for Studying Cell Response to Mechanical Stimulation", Exp. Cell Research, vol. 109 (1977), pp. 285–298.
Takeuchi, "Wound Healing in the Cornea of the Chick Embryo", Developmental Biology, vol. 70 (1979), pp. 232–240.
Vandenburgh, "A Computerized Model System for Studying the Effects of Mechanical Activity on Cell Growth In Vitro", Program Abstracts 28th Am. Meeting of the Tissue Culture Ass. May 27–31, 1987.
Vandenburgh, "Dynamic Mechanical Orientation of Skeletal Myofibers in Vitro", Developmental Biology, vol. 93 (1982), pp. 438–443.
Vandenburgh et al., "In Vitro Model for Stretch-Induced Hypertrophy of Skeletal Muscle", Science, vol. 23 (1979), pp. 265–268.

Primary Examiner—Robert J. Warden
Assistant Examiner—William H. Beisner
Attorney, Agent, or Firm—Salter, Michaelson & Benson

[57] ABSTRACT

An apparatus for growing tissue specimens in vitro includes an expandable membrane for receiving a tissue specimen thereon, a mechanism for expanding the membrane and the tissue specimen, and a controller for controlling the expanding mechanism. The controller is operative for applying an activity pattern to the membrane and a tissue specimen thereon which includes simultaneous continuous stretch activity and repetitive stretch and release activity. The continuous stretch activity and the repetitive stretch and release activity simulate the types of activity to which cells are exposed in vivo due to growth and movement, respectively, and they cause the cells of tissue speciments grown in the apparatus to develop as three-dimensional structures similar to those grown in vivo.

15 Claims, 4 Drawing Sheets

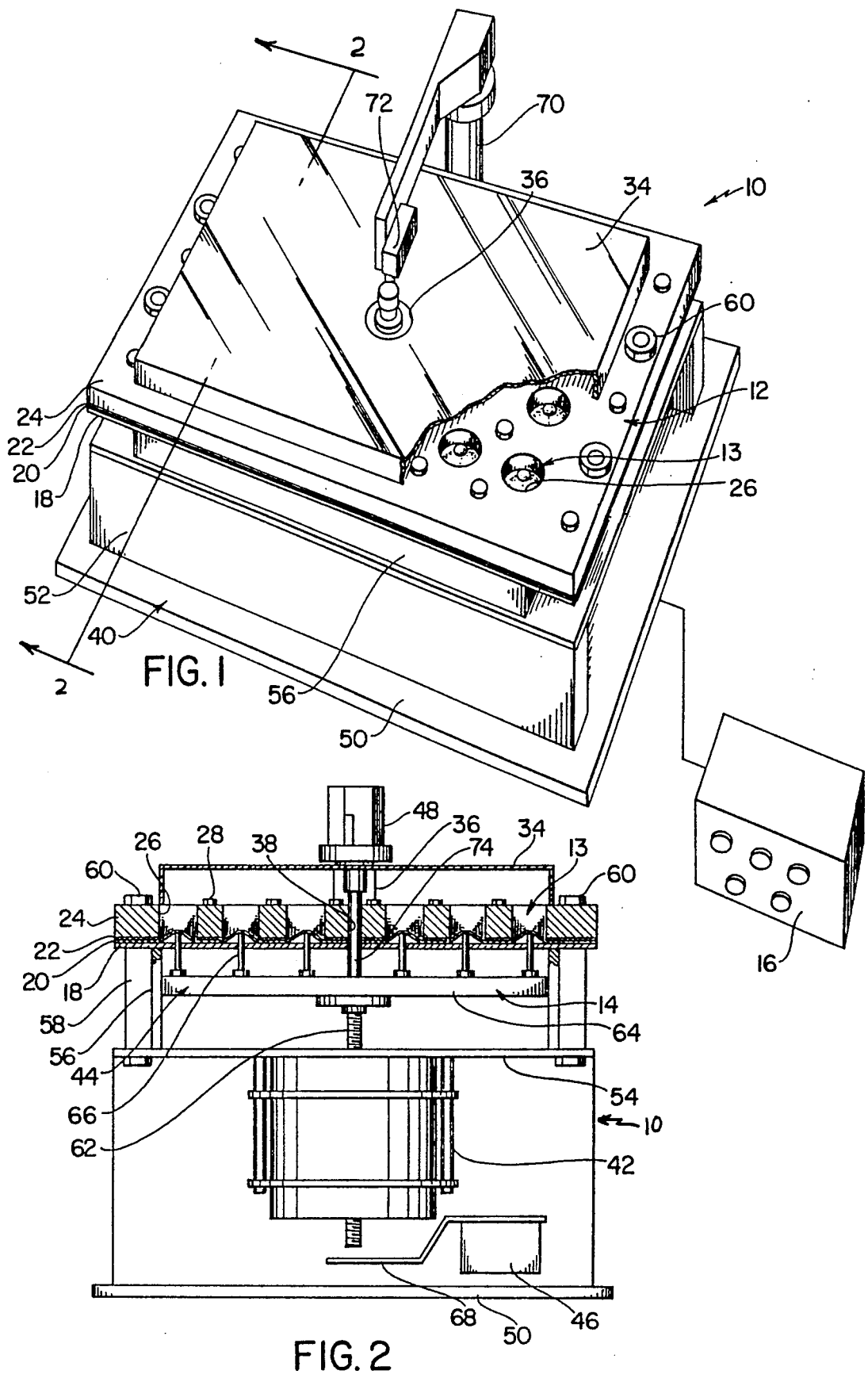

APPARATUS FOR GROWING TISSUE SPECIMENS IN VITRO

This is a division of U.S. Pat. No. 4,940,853, issued on Jul. 10, 1990.

BACKGROUND AND SUMMARY OF THE INVENTION

The instant invention relates to tissue cultures and more particularly to an in vitro method and apparatus for growing tissue cells under conditions which more closely resemble cells grown in vivo.

Experiments wherein tissue cells are grown in in vitro tissue cultures have produced significant amounts of data relating to tissue development over the past 70 years. However, it has generally been found that the cells of specimens which are grown in static, in vitro environments develop as randomly oriented embryonic cells which lack the three-dimensional adult characteristics of cells grown in vivo. Recently, however, it has been found that by applying stimulation consisting of gradual stretching forces to tissue specimens grown in in vitro tissue cultures, the tissue cells thereof tend to align with the stretching forces and they therefore exhibit somewhat more mature characteristics. However, it has been found that even the cells of specimens which are exposed to stimulation consisting of gradual stretching forces fail to develop into adult-like, three-dimensional structures which are similar to those grown in vivo. It has also recently been found that by applying stimulation consisting of repetitive or reciprocating stretch and release activity to tissue specimens grown in in vitro tissue cultures, the cells thereof tend to align in perpendicular relation to the direction of the stretch and release activity, and still fail to develop into three-dimensional structures similar to those grown in vivo.

It has now been found that when in vitro culture cells are stimulated by applying a mechanical activity pattern thereto which more closely resembles the type of stimulation pattern which naturally occurs in vivo, it is possible to grow the cells of a tissue specimen into structures which more closely resemble tissue cells grown in vivo. Specifically, it has been found that by simultaneously applying both continuous, gradual stretch activity and periodic reciprocal stretch and release activity to a tissue specimen grown in an in vitro culture, it is possible to develop the cells of the tissue specimen into well formed, three-dimensional structures which are similar to those grown in vivo. In this connection, by continuously stretching a tissue specimen, the tissue specimen is subjected to the type of mechanical stimulation which normally results from animal growth in vivo; and by periodically repetitively stretching and releasing the tissue specimen, the tissue specimen is subjected to the type of stimulation to which in vivo tissue cells are exposed during animal movements.

In accordance with the above, the method of the subject invention comprises the steps of supporting a tissue specimen in the gross morphology found in vivo (aligned or unaligned as in vivo) with an expandable membrane so that the tissue specimen is expandable therewith, maintaining the tissue specimen in an extracellular matrix, such as a collagen matrix, maintaining the tissue specimen in a life support environment, periodically supplying fresh nutrients to the tissue specimen, and gradually stretching the membrane by at least approximately 0.5% over a 24 hr period while periodically reciprocally stretching and releasing the membrane by at least approximately 0.01% for a total of at least 60 seconds during the course of the same 24 hr period. The tissue specimen is preferably stretched and released by between 0.02% and 60% during the stretch and release activity periods, and the stretch and release activity periods preferably last at least approximately 5 seconds. The stretch and release activity periods are preferably separated by rest periods of at least approximately 5 seconds, and the tissue specimen is preferably gradually and continuously stretched at a rate of between 0.005 mm/hr and 1.0 mm/hr. The membrane preferably has a pair of spaced, upwardly extending support walls thereon which are made of a biocompatible material and have opposed support surfaces thereon, and the tissue specimen is preferably allowed to attach to the support surfaces of the support walls, and it is stretched by moving the support walls apart.

When the method of the subject invention is applied to a tissue specimen comprising isolated cells requiring alignment, the tissue specimen is preferably applied to a resiliently expandable membrane which is adapted to permit attachment of the tissue specimen thereto, such as by preapplying a collagen coating thereto. Thereafter, the method is carried out by maintaining the tissue specimen in a life support environment, periodically feeding the tissue specimen, and maintaining the cells of the tissue specimen in an extracellular matrix sufficient to permit stretching of the tissue specimen without causing damage thereto. Then, while maintaining these conditions, the membrane is gradually stretched over a prolonged period of time until the cells are substantially aligned in the direction of stretch, and thereafter the membrane is gradually stretched by at least approximately 0.5% over the course of a 24 hr period while it is periodically stretched and released by at least approximately 0.01% for a total of at least 60 seconds during the course of the same 24 hr period. The tissue specimen is preferably stretched and released by between 0.02% and 60% during the stretch and release activity periods, and it is preferably gradually stretched at a rate of between 0.005 mm/hr and 1.0 mm/hr. The tissue specimen is preferably repetitively stretched and released during activity periods of at least 5 seconds in duration, and the activity periods are preferably separated by rest periods of at least five seconds in duration. The membrane preferably has a pair of spaced, upwardly extending support walls thereon, and the support walls are preferably made of a biocompatible material and they have opposed support surfaces thereon. The support walls are preferably made of stainless steel screening so that the support surfaces thereof have sufficiently roughened textures to permit attachment of the cells thereto. In this regard, the tissue specimen is attached or allowed to attach to the support surfaces of the support walls, and thereafter the tissue specimen is mechanically stimulated by stretching the membrane to move the support walls apart in accordance with the method.

The apparatus of the instant invention which is operative for performing the above method comprises a resiliently expandable support means which is operative for supporting a tissue specimen and adapted as needed to permit attachment of the tissue specimen thereto. The apparatus further comprises means for expanding the support means to stretch the tissue specimen and control means for controlling the means for expanding the support means to gradually and substantially continuously expand the support means over a prolonged period of time and to repetitively expand or stretch and release the support means over the same period of time. The control means is preferably adapted to control the means for expanding the support means to effect stretching activity in accordance with the method as hereinabove set forth. In a first embodiment of the apparatus, the support means comprises a substantially circular, resiliently flexible membrane having an upwardly facing side and a downwardly facing side, and the tissue specimen is applied to the upwardly facing side of the membrane. In this embodiment, the mechanical manipulating means is engageable with the downwardly facing side of the membrane to deform the membrane upwardly. The support means preferably further comprises a substantially circular support ring on the membrane which extends upwardly from the membrane and has an inwardly facing support surface thereon. The support ring is made of a biocompatible material, such as stainless steel screening, and it has a sufficiently roughened surface texture to permit attachment of the tissue specimen thereto. In a second embodiment of the apparatus, the support means comprises a resiliently flexible membrane having opposite first and second ends and having an upwardly facing side and a downwardly facing side, and the mechanical manipulating means is operative for stretching the cells by separating the first and second ends. In this embodiment, the support means preferably further comprises first and second spaced support walls which extend upwardly from the upwardly facing side of the membrane and have opposed support surfaces thereon. The support walls are also preferably made of a biocompatible screening material, such as stainless steel screening, so that the support surfaces have sufficiently roughened textures to permit attachment of the tissue specimen thereto.

Accordingly, it is a primary object of the instant invention to provide an effective method of growing a tissue specimen in vitro so that the tissue specimen more closely resembles tissue which is grown in vivo.

Another object of the instant invention is to provide a method of mechanically stimulating the growth of a tissue specimen by gradually and substantially continuously stretching the tissue specimen over a prolonged period of time while simultaneously repetitively stretching and releasing the tissue specimen.

Another object of the instant invention is to provide an apparatus for mechanically stimulating the growth of a tissue specimen.

An even further object of the instant invention is to provide an effective apparatus for mechanically stimulating the growth of a tissue specimen by simultaneously gradually stretching the tissue specimen and periodically repetitively stretching and releasing the tissue specimen.

Other objects, features and advantages of the invention shall become apparent as the description thereof proceeds when considered in connection with the accompanying illustrative drawings.

BRIEF DESCRIPTION OF THE DRAWINGS

In the drawings which illustrate the best mode presently contemplated for carrying out the present invention:

FIG. 1 is a fragmentary perspective view of a first embodiment of the apparatus of the instant invention;

FIG. 2 is a sectional view taken along line 2—2 in FIG. 1;

DESCRIPTION OF THE INVENTION

Figure 3:
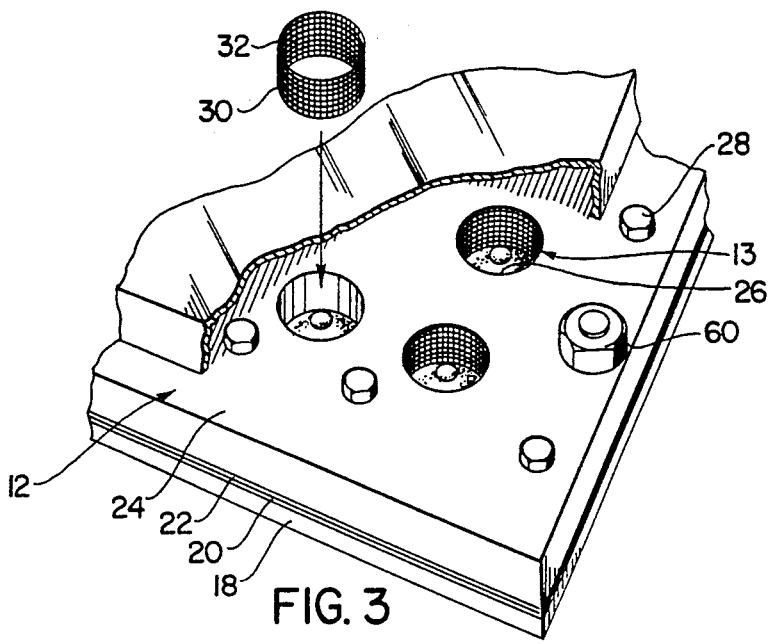
FIG. 3 is an enlarged, fragmentary, exploded perspective view of the cell assembly of the apparatus illustrated in FIG. 1.

Referring now to the drawings, a first embodiment of the apparatus for growing tissue specimens of the instant invention is illustrated in FIGS. 1–4 and generally indicated at 10 in FIGS. 1 and 2. The apparatus 10 comprises a well assembly generally indicated at 12 having a plurality of wells 13 therein, a stimulator pin assembly generally indicated at 14, and a controller 16. For operation of the apparatus 10, living tissue cells are placed in the wells 13 in the well assembly 12, and the controller 16 is actuated to control the stimulator pin assembly 14 to mechanically stimulate the tissue cells with an activity pattern which includes both gradual, substantially continuous stretch activity and repetitive stretch and release activity.

The well plate assembly 12 comprises a bottom plate 18 having a plurality of spaced apertures therein, a membrane 20, a gasket 22, and an upper plate 24. The membrane 20 is preferably made of a medical grade, resiliently flexible, rubberized material, such as Silastic (Dow Corning Corp. TM), and it preferably has a thickness of approximately 0.01 in. The upper surface of the membrane 20 is preferably precoated with an extracellular matrix material, such as rat tail collagen, to adapt the membrane 20 to permit the attachment of tissue cells thereto. The gasket 22 has a plurality of spaced bores therein, and it is received on the membrane 20 and adhesively secured thereto with a silicone rubber sealant so that the bores in the gasket 22 are substantially aligned with the apertures in the bottom plate 18. The upper plate 24 is preferably made of Teflon (DuPont TM), and it has a plurality of bores 26 therein which are substantially aligned with the bores in the gasket 22. The upper plate 24, the gasket 22, the membrane 20, and the bottom plate 18 are maintained in assembled relation with bolts 28. Also included in the well assembly 12 is a plurality of support rings 30 which are received in the wells 13, the rings 30 having roughened inner support surfaces 32 thereon which have sufficient roughness to permit attachment of tissue cells thereto. The rings 30 are preferably made of a biocompatible screening material, such as stainless steel screening, and they are formed so that they are frictionally retained against the sidewalls of the wells 13. The support rings 30 are preferably made of screening having between 4×4 meshes/in and 250×250 meshes/in, a wire diameter of between 0.31 mm and 3.76 mm, and mesh openings of between 0.20 mm and 2.59 mm; and as herein embodied, they have 50×50 meshes/in, a wire diameter of 0.31 mm, and mesh openings of 0.20 mm. The rings 30 are received in the wells 13 so that they are positioned on the membrane 20 and extend upwardly along the inner sides of the bores in the gasket 22 and the bores 26 in the upper plate 24. Also included in the well assembly 12 is a cover 34 which is preferably made of a clear, plastic material and is receivable on the Teflon plate 24 so that it covers the wells 13. The cover 34 has a centrally disposed tubular sleeve 36 formed therein which extends downwardly to the plate 24; and a passage 38 which is substantially aligned with the sleeve 36 extends downwardly through the upper plate 24, the gasket 22, and the membrane 20 to the stainless steel plate 18.

The stimulator pin assembly 14 comprises a base 40, a stepping motor 42, a pin plate assembly generally indicated at 44, a lower limit switch assembly 46, and an upper limit switch assembly 48. The base 40 comprises a substantially flat bottom base plate 50 having a pair of spaced, upwardly extending sidewalls 52 thereon, support plate 54 which is received and secured on the upper ends of the sidewalls 52, and an upper sidewall frame 56 on the support plate 54. The well assembly 12 is received on the upper ends of the upper sidewall frame 56, and it is secured to the support plate 54 with threaded rods 58 having nuts 60 thereon. The stepping motor 42 preferably comprises a 4-phase, linear actuator stepping motor, such as a Model LAS motor made by Hurst Manufacturing Corp. of Princeton Ind., and it is mounted on the support plate 54. The motor 42 includes a threaded shaft 62 which is connected to the pin plate assembly 44, and it is actuatable to linearly move the shaft 62 in minute-stepped increments in order to raise or lower the pin plate assembly 44 in a substantially continuous motion and/or a repetitive motion. The pin plate assembly 44 includes a main plate 64 which is attached to the shaft 62, and a plurality of pins 66 which extend upwardly from the main plate 64. The main plate 64 is attached to the shaft 62, and it is contained within the sidewalls 56 to prevent it from rotating as the shaft 62 is linearly moved, although it is freely movable upwardly therewith. The pins 66 have blunt upper ends, and they are positioned on the plate 64 so that they pass through the apertures in the plate 18, and they are substantially aligned with the centers of the wells 13 as illustrated. Accordingly, the pins 66 are engageable with the membrane 20 in the wells 13 to flex or expand the membrane 20 upwardly in the center portions of the wells 13. The lower limit switch 46 is of conventional construction, and it includes an arm 68 which is engageable with the lower end of the shaft 62 so that it defines a lower limit position for the shaft 62. The upper limit switch assembly 48 includes an arm assembly 70 which is mounted on the base 40 and a limit switch element 72 on the arm assembly 70. The arm assembly 70 is pivotable outwardly to enable the cover 34 to be removed, and it is also positionable in the manner illustrated in FIGS. 1 and 2, wherein the limit switch element 72 is substantially aligned with the sleeve 36. The limit switch assembly 48 also includes a shaft 74 which extends downwardly through the sleeve 36 and the passage 38 and rests on the main pin plate 64 so that it moves upwardly with the main pin plate 64 and is engageable with the switch element 72 for defining an upper limit position for the pin plate 64.

Figure 5:
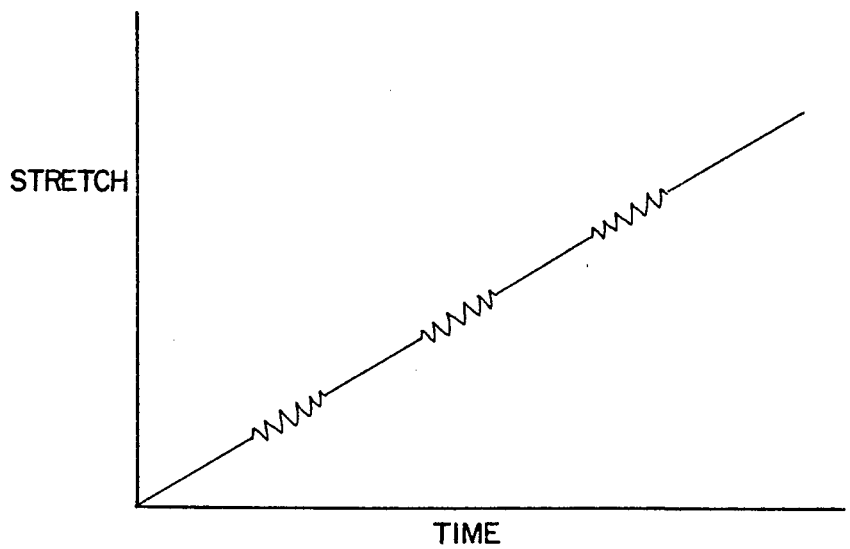
FIG. 5 is a graph illustrating a typical activity pattern applied by the method.

The controller 16 preferably comprises a computer, such as an Apple IIe computer, which is interfaced with the stepping motor 42 through a digital interface card (DI09, Interactive Structures, Inc., Malvern, Pa.) and optical data links (UI16 Isolated Power Interface System with 4 DC-0 Output Modules, Interactive Structures). The controller 16 is operative for controlling the stepping motor 42 to produce various predetermined activity patterns, such as the pattern illustrated in FIG. 5. In this connection, the controller 16 is preferably operated to control the motor 42 for gradually and substantially continuously stretching the membrane 20 by advancing the pin plate assembly 44 upwardly in minute-stepped increments over a prolonged period of time and for also periodically repetitively stretching and releasing the membrane 20 by reciprocally moving the pin plate assembly 44 upwardly and downwardly at predetermined intervals during the same period of time.

Figure 4:
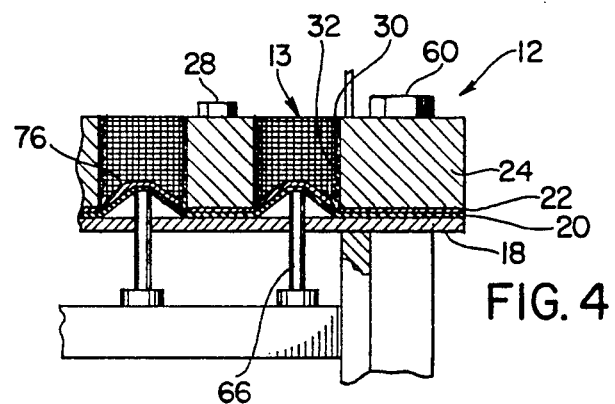
FIG. 4 is an enlarged sectional view of the well assembly with tissue specimens in the wells.

For use and operation of the apparatus 10, tissue specimens 76 illustrated in FIG. 4 are placed on the membrane 20 in the wells 13. The tissue specimens may comprise various types of living tissue, such as various types of nerve or muscle tissue, and they are prepared and applied to the membrane 20 in accordance with conventional laboratory techniques. After the tissue specimens 76 have been plated on the membrane 20, the apparatus 10 is placed in a humidified incubator to maintain the tissue specimens 76 in a life support environment, and the tissue specimens 76 are allowed to attach to the membrane 20 and/or support ring 30. A suitable nutrient medium is periodically supplied to the specimens 76; and the specimens 76 are maintained in a sufficient extracellular matrix to prevent damage thereto during stretching by applying additional collagen or another suitable matrix material thereto if and when needed as determined by known techniques. In this connection, with some types of tissue cells, such as skeletal muscle cells, it is necessary to apply a matrix, such as a collagen gel, to provide sufficient support for the cells during stretching; although, with some other types of tissue cells, such as some nerve cells which are capable of producing sufficient quantities of extracellular matrix material, externally applied matrices are not required. In any event, after the tissue specimens 76 are attached to the membrane 20 and/or support ring 30, which may take up to 24 hrs in the case of isolated tissue cells, the controller 16 is actuated to control the stepping motor 42 to gradually and substantially continuously stretch the tissue specimens 76 over a prolonged period of time while periodically repetitively stretching and releasing the tissue specimens 76 at spaced intervals during the same period of time. With certain types of tissue specimens, during this portion of the method the tissue specimens actually attach themselves to the rings 30 and detach themselves from the membrane 20 so that the rings 30 actually support the tissue. In this connection, it has been found that when some tissue specimens attach themselves to the rings 30, they actually become interwoven in the wire mesh of the rings 20 so that they are capable of withstanding stretching activity without being separated from the rings 30. In any event, during this portion of the method, the tissue specimens are preferably repetitively stretched and released by between 0.02% and 60%, and they are preferably simultaneously continuously stretched at a rate of between 0.005 mm/hr and 1.0 mm/hr. The stretch and release activity periods preferably last for at least approximately 5 seconds and they are preferably separated by a rest period of at least approximately 5 seconds in duration; and this procedure is preferably carried out for at least several days. It has been found that by following this procedure, the apparatus 10 can be effectively utilized for growing adult-like tissue which are similar to tissue grown in vivo; although, in the case of aligned cells, the cells are generally oriented so that they extend substantially radially outwardly from the centers of the wells 13.

Figure 9:
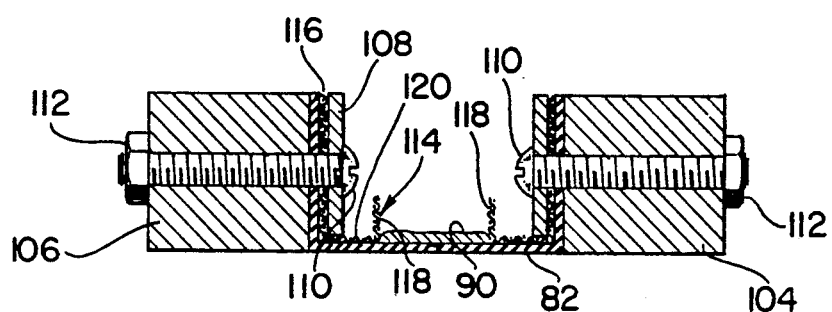
FIG. 9 is an enlarged sectional view taken along line 9—9 in FIG. 8 with tissue specimens in the wells.

A second embodiment of the apparatus of the instant invention is illustrated in FIGS. 6–9 and generally indicated at 78. The apparatus 78 comprises a base 79, an expandable well assembly 80 having a plurality of wells generally indicated at 82 therein which is mounted on the base 79, a control well assembly 84 which is also mounted on the base 79, a stepping motor 86 and a controller 88. For use and operation of the apparatus 78, the controller 88 is operated to control the motor 86 for expanding the well assembly 80 so that the wells 82 are gradually and substantially continuously stretched over a prolonged period of time and also periodically repetitively stretched and released during the same period of time. Accordingly, when tissue specimens 90 illustrated in FIG. 9 are applied to the wells 82 and the wells 82 are stretched, the tissue specimens 90 are subjected to an activity pattern which is similar to that illustrated in FIG. 5 so that the cells in the tissue specimens 90 develop into adult-like structures which are similar to cells grown in vivo.

Figure 6:
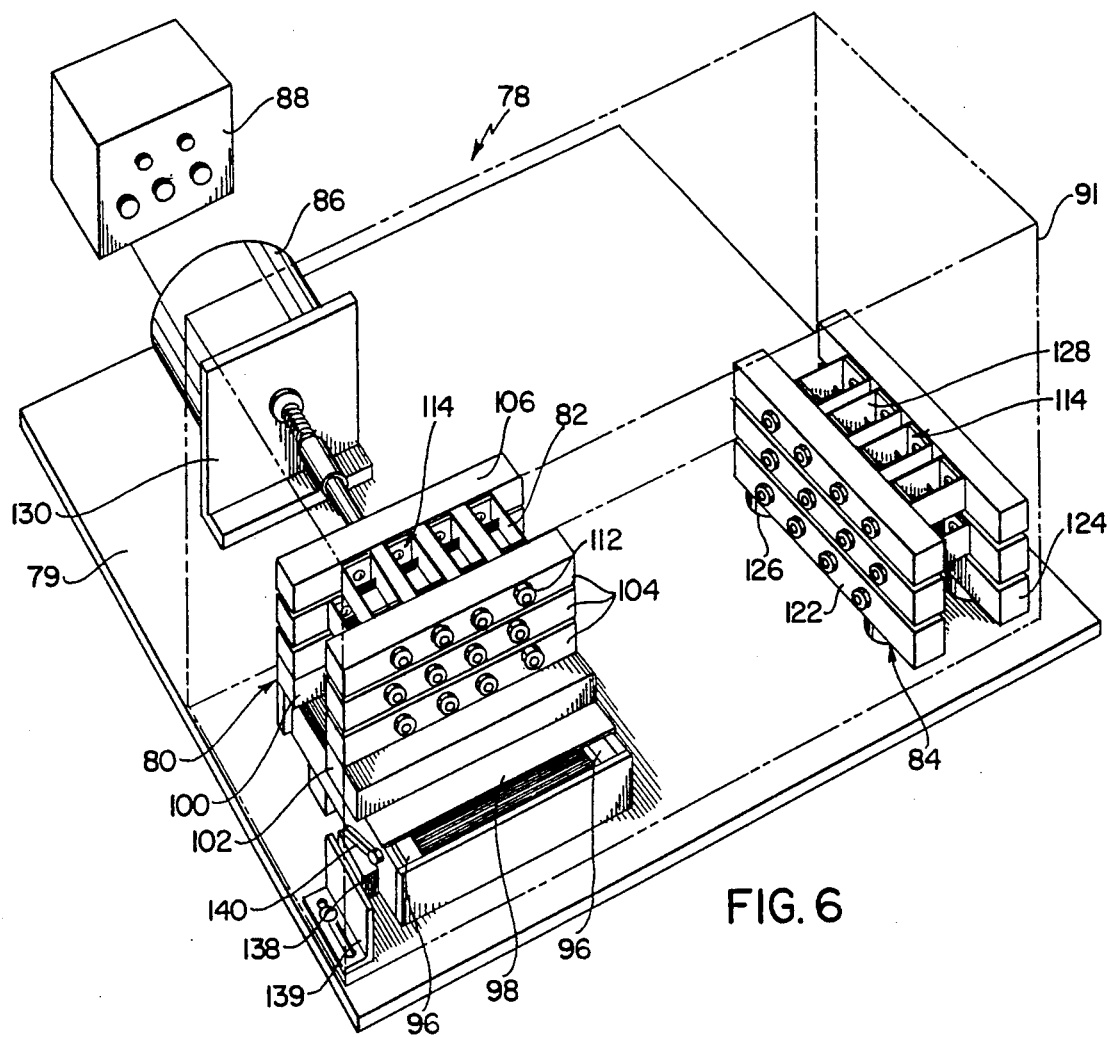
FIG. 6 is a perspective view of a second embodiment of the apparatus.
Figure 7:
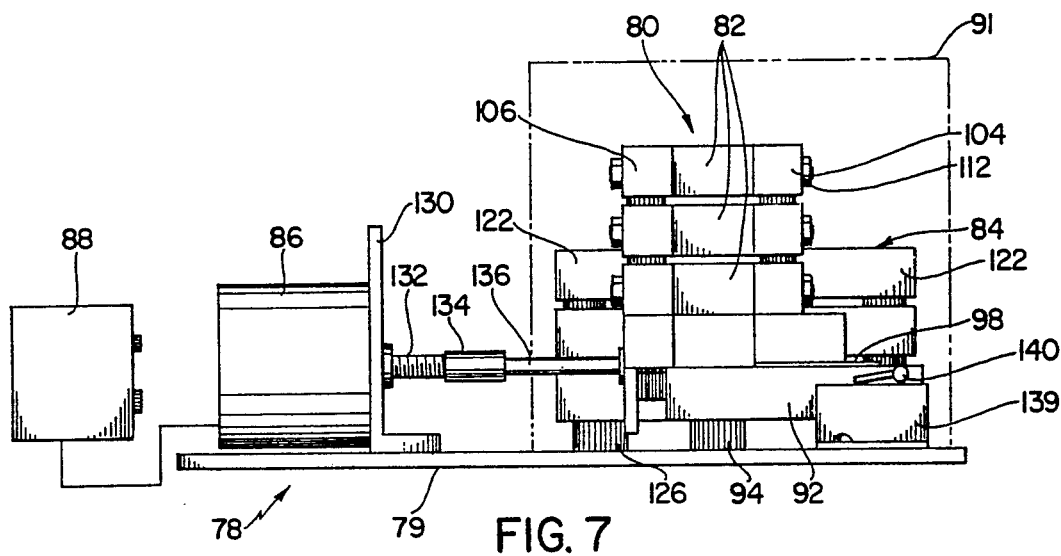
FIG. 7 is an end elevational view thereof.
Figure 8:
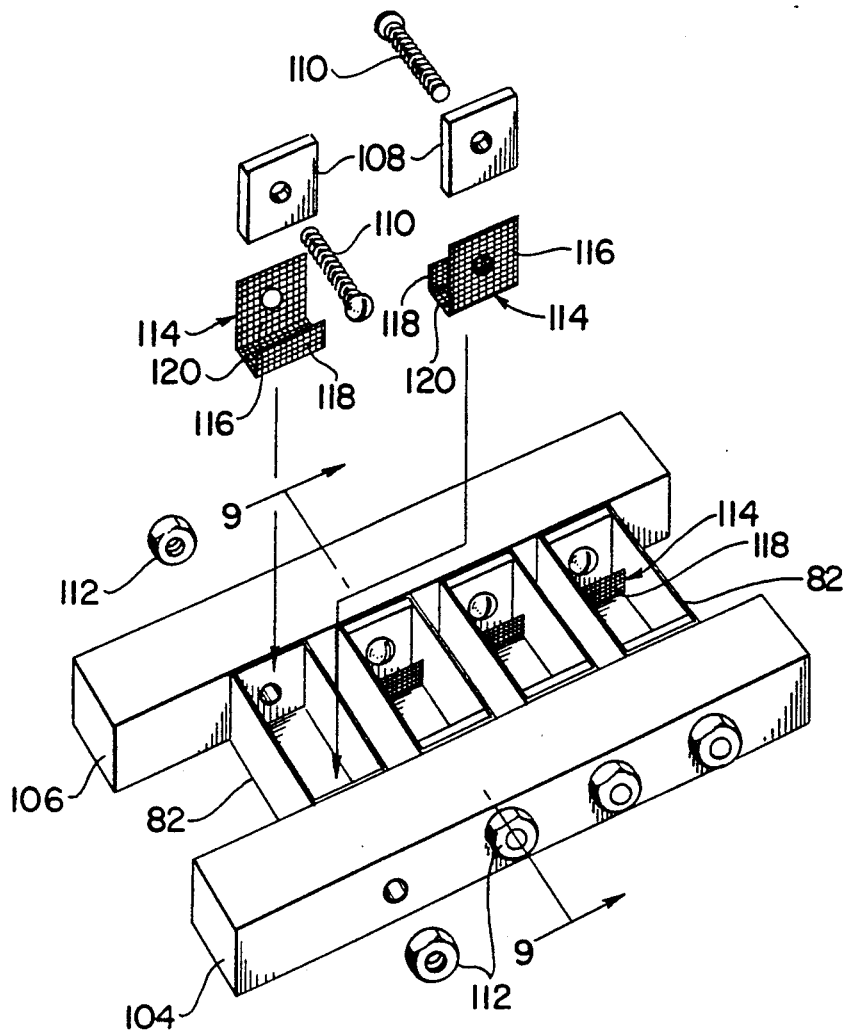
FIG. 8 is an exploded fragmentary perspective view of the well assembly thereof.

The base 79 comprises a substantially flat metal plate; and it is operative for supporting the expandable well assembly 80, the control well assembly 84 and the stepping motor 86 as illustrated most clearly in FIG. 6. A cover 91, which is preferably made of a transparent plastic material, is received on the base for covering the well assembly 80.

The expandable well assembly 80 comprises a frame 92 which is secured in a fixed position on the base 79 with a plurality of frame mounts 94. The well assembly 80 further comprises a pair of ball bearing roller tracks 96 which extend forwardly along opposite sides of the frame 92 and a movable stage 98 which is mounted so that it can travel freely on the tracks 96. A rear spacer bar 100 is mounted in a fixed position on the frame 92, and a front spacer bar 102 is mounted on the stage 98. A plurality of stacked rear well end bars 106 are mounted as a unit on the rear spacer bar 100, and a plurality of stacked front well end bars 104 are mounted as a unit on the front spacer bar 102. In this connection, the well end bars 104 and 106 are mounted in substantially parallel relation in spaced pairs; and since the front well end bars 104 are mounted on the front spacer bar 102 which is in turn mounted on the stage 98, the front well end bars 104 are movable with the stage 98 in substantially parallel relation to the rear well end bars 106. The wells 82 are illustrated most clearly in FIGS. 8 and 9 and they comprise substantially rectangular, open box-like structures which are made from a resiliently expandable rubberized material, such as Silastic (Dow Corning Corp. TM). The wells 82 are positioned between the front and rear well end bars 104 and 106, respectively, and they are secured to the well end bars 104 and 106 with Teflon (DuPont TM) plates 108 and screws 110 having nuts 112. The plates 108 are preferably of substantially the same dimension and configuration as the ends of the rectangular wells 82 so that the side and bottom walls of the wells 82 can be stretched while nevertheless maintaining the wells 82 in substantially rectangular configuration. The bottom surfaces of the wells 82 are preferably coated with an extracellular matrix material, such as collagen, to adapt the bottom surfaces of the wells 82 to permit the cells of tissue specimens to attach themselves if required thereto. Support screens generally indicated at 114 having rear walls 116 are secured in the wells 82 by the plates 108 so that the rear walls 116 are captured between the plates 108 and the ends walls of the wells 82, as illustrated most clearly in FIG. 9. The support screens 114 further include front walls 118 which are joined to the rear walls 16 with bottom walls 120 so that the front walls 118 extend upwardly in spaced relation to their respective rear walls 116. A pair of the support screens 114 are received in each of the wells 82, and the support screens 114 are dimensioned so that the front walls 118 of the support screens 114 in each well 82 are disposed in spaced relation as illustrated in FIG. 9. The support screens 114 are preferably made of a biocompatible screening material, such as stainless steel screening, and they preferably have mesh sizes of between $4 \times 4$ meshes/in and $250 \times 250$ meshes/in, and as herein embodied, they have a mesh size of $50 \times 50$ meshes/in. The support screens 114 are preferably made from wire having a diameter of between 0.31 mm and 3.76 mm, and they preferably have mesh openings of between 0.20 mm and 2.59 mm. As herein embodied, the support screens 114 are made from wire having a diameter of 0.31 mm, and they have mesh openings of 0.20 mm.

The control well assembly 84 comprises a plurality of stacked left well end bars 122 and a plurality of stacked right well end bars 124 which are secured to the base 79 with mounts 126 so that the bars 122 and 124 are in spaced, substantially parallel pairs and a plurality of wells 128 which are secured to the well end bars 122 and 124. The wells 128 are substantially identical to the wells 82, and they include support screens 114 and Teflon plates 108. However, because the well end bars 122 and 124 are mounted in spaced relation at fixed positions on the base 79, the control well assembly 84 cannot be operated to expand the wells 128.

The motor 86 preferably comprises a Hurst model LAS stepping motor made by the Hurst Manufacturing Corp. of Princeton Ind., and it is mounted on the base 79 with a bracket 130. The motor 86 includes a threaded, shaft 132 which is connected to the stage 98 through a nonrotatable female threaded sleeve 134 and a fixed shaft 136. Accordingly, when the motor 86 is actuated to linearly move the threaded shaft 132, the sleeve 134 is longitudinally advanced with the threaded shaft 132 to advance the stage 98. A limit switch 138 is mounted on the base 79 adjacent the forward end of the frame 92 with a bracket 139, and a limit switch trip 140 is attached to the forward end of the stage 98. The limit switch 138 is connected to the motor 86 so that it is operative for deenergizing the motor 86 when the stage 98 has reached a predetermined limit of its forward travel.

The controller 88 is operative for controlling the operation of the motor 86 to apply a predetermined pattern of stretch activity to the specimens 90 in the wells 82. The controller 88 preferably comprises an Apple IIe computer which is interfaced with the stepping motor 86 through a digital interface card, via optical data links.

For use and operation of the apparatus 78 in accordance with the method of the subject invention, tissue specimens are positioned on or next to the bottom surfaces of the wells 82 and 128 between the front support walls 118 therein, and the tissue specimens are maintained in a life support environment and periodically fed nutrients over the course of the method. The tissue specimens are attached or allowed to attach to the membranes defined by the collagen-coated bottom surfaces of the wells 82 and 128 or the support walls 118. Thereafter, in the case of tissue specimens which require cellular alignment, the controller 88 is operated to control the motor 86 to move the stage 98 and the front well end bars 104 slowly forwardly to gradually and substantially continuously stretch the tissue specimens in the wells 82 until the cells thereof are substantially aligned. In any event, thereafter, the tissue specimens are maintained in a sufficient extracellular matrix to prevent tearing of the tissue specimens during stretching. In this regard, again, a sufficient matrix may occur naturally for some types of cells, but alternatively a sufficient matrix may be achieved by applying an effective amount of a known matrix material, such as a collagen, to the tissue specimens. Thereafter, the tissue specimens are gradually and substantially continuously stretched over a prolonged period of time and they are periodically repetitively stretched and released during the same period of time. In this connection, it has been found that in some cases at this point in the method tissue specimens which have been applied to the membrane begin to attach themselves to the front support walls 118, and they become detached from the collagen-coated bottom surfaces of the wells 82; and after the tissue specimens have been exposed to continuous and repetitive stretch activity for several days, the cells in the tissue specimens actually become fully attached to the front support walls 118 and completely detached from the bottom surfaces of the wells 82. The tissue specimens are preferably stretched and released by between approximately 0.02% and 60% during the stretch and release activity periods, and they are preferably gradually and substantially continuously stretched at a rate of between 0.005 mm/hr and 1.0 mm/hr. Further, the activity periods preferably last for at least 5 seconds and they are preferably separated by rest periods of at least 5 seconds in duration during which the tissue specimens are only subjected to gradual, substantially continuous stretch activity.

It has been found that when tissue specimens are mechanically stimulated in the apparatus 78 in the manner hereinabove set forth, the cells thereof develop into three-dimensional tissues, which have the appearance of natural tissues grown in vivo. In contrast, it has been found that when tissue specimens are grown in the control well assembly 84 they do not develop into mature-like in vivo tissues.

EXAMPLE

In a specific example of the method of the instant invention, embryonic avian skeletal muscle cells comprising pectoralis muscle cells from 11 to 12 day old in ovo chick embryos were minced into pieces, prepared by conventional techniques and plated onto the collagen-coated bottom walls of the wells 82 of the apparatus 78. The apparatus 78 had support screens 114 therein which were made of 0.31 mm stainless steel wire, and they had 50×50 meshes/in with 0.2 mm mesh openings. The apparatus 78 was thereafter maintained in a humidified 5% $CO_2$ incubator at 37.2° C. throughout the experiment. During the second day of the experiment the tissue specimens were fed fresh nutrient, and the controller 88 was actuated to slowly and continuously stretch the wells 82 and the tissue specimens therein at a rate of approximately 8 mm/24 hr. On the third day the specimens were again supplied fresh nutrient, and the continuous stretch activity was continued until the specimens had been stretched for a total of approximately 36 hrs. By the end of the third day, the muscle cells had become substantially aligned in the direction of the stretching activity, and on the fourth day the specimens were embedded in a collagen gel extracellular matrix. On the fifth and sixth days, the tissue specimens were again supplied fresh nutrients; and on the seventh day the tissue specimens were supplied fresh nutrients, and the controller 88 was actuated to apply substantially continuous stretch activity to the wells 82 at a rate of approximately 1 mm/24 hrs and to simultaneously apply repetitive stretch activity to the wells 82, stretching and releasing the tissue specimens by 1 mm five times during a 20-second period, and then resting the tissue specimens by discontinuing only the repetitive activity for a 10-second period. This same pattern of repetitive stretch activity was applied three times, and then the tissue specimens were allowed to rest for a 30-minute period during which only continuous stretch activity was applied. The same repetitive stretch activity pattern was then repeated throughout the course of the seventh day. On the eighth and ninth days, the specimens were again supplied fresh nutrients and the repetitive and continuous stretch activity patterns were continued, and on the tenth day the specimens were fully rested by applying no stretch activity thereto. It was noted that after the eleventh day, the cells of the specimens had become fully attached to the support walls 118, and that they had completely detached themselves from the membrane surfaces of the wells 82 so that the support walls 118 were able to function as artificial tendons which applied stretch activity to the tissue specimens. From the eleventh to the eighteenth day, the tissue specimens were subjected to only repetitive stretch activity, wherein the tissue specimens were stretched by 2 mm and relaxed five times during a 20-second period and then allowed to rest for 10 seconds. This pattern was repeated three times and then the tissue specimens were allowed to rest for 30 minutes, and thereafter the entire pattern was repeated until the end of the eighteenth day.

It was found that after eighteen days the tissue specimens which had originally been a monolayer of cells approximately 22 mm in length had been stretched to 35.5 mm in length and that the muscle fibers in the tissue specimens were aligned and organized in three-dimensional muscle fasicles. Further, these muscle fibers appeared very similar to mature in vivo muscle fibers.

It is seen therefore that the instant invention provides an effective apparatus and method for stimulating tissue growth in vitro. The apparatus 10 and 78 are operative in accordance with the method for simultaneously applying stretch activity patterns to tissue specimens which simulate the types of activity patterns to which in vivo tissue is exposed as a result of normal growth and periodic movement. It has been found that this type of mechanical stimulation causes tissue cells to form into natural and more mature tissue which closely resembles cells developed in vivo. Accordingly, it is seen that the method and apparatus of the instant invention represent significant advancements in the biological art which have substantial medical and scientific significance.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. An apparatus for growing a tissue specimen in vitro comprising:
   (a) expandable support means for supporting the tissue specimen and constructed so as to permit attachment of the tissue specimen thereto, said support means being expandable to effect stretching of the tissue specimen;
   (b) means for mechanically expanding said support means to stretch the tissue specimen; and
   (c) control means for controlling said mechanical expanding means to both gradually and substantially continuously expand said expandable support means over a prolonged period of time and to simultaneously repetitively expand and release said expandable support means over said period of time.

2. The apparatus of claim 1, wherein said control means controls said mechanical expanding means so as to expand and release said expandable support means by between 0.02% and 60% during said expand and release activity.

3. The apparatus of claim 1, wherein said control means controls said mechanical expanding means so as to periodically repetitively stretch and release the tissue specimen during activity periods of at least approximately five seconds duration.

4. In the apparatus of claim 3, said activity periods being separated by rest periods of at least approximately five seconds duration during which the tissue specimen is subjected to said gradual and substantially continuous stretch activity but not subjected to significant stretch and release activity.

5. In the apparatus of claim 1, said control means controlling said mechanical expanding means to gradually and substantially continuously stretch the tissue specimen at a rate of between 0.005 mm/hr and 1.0 mm/hr.

6. In the apparatus of claim 1, said support means comprising a substantially circular resiliently flexible membrane having an upwardly facing side and a downwardly facing side, said support means being operative for supporting the tissue specimen on the upwardly facing side of said membrane, said expanding means engaging the downwardly facing side of said membrane to deform said membrane and to thereby stretch the tissue specimen.

7. In the apparatus of claim 6, said support means further comprising a substantially circular support ring on said membrane extending upwardly from the upwardly facing side thereof, said support ring having an inwardly facing attachment surface thereon which has a sufficiently roughened texture to permit attachment of the tissue specimen thereto.

8. In the apparatus of claim 7, said support ring comprising a ring of screening which substantially defines the inwardly facing attachment surface thereof, said ring of screening being made of a biocompatible material.

9. In the apparatus of claim 8, said ring of screening being made of stainless steel.

10. In the apparatus of claim 8, said ring of screening having between 4×4 and 250×250 meshes/in, having a wire diameter of between 0.04 mm and 3.76 mm, and a mesh opening width of between 0.06 mm and 2.6 mm.

11. In the apparatus of claim 1, said support means comprising a flexible membrane having opposite first and second ends and having an upwardly facing side and a downwardly facing side, said mechanical expanding means being operative for stretching said membrane by separating said first and second ends.

12. In the apparatus of claim 11, said support means further comprising first and second support walls extending upwardly from the upwardly facing side of said membrane, said first and second support walls having first and second substantially opposed attachment surfaces thereon, respectively, which have sufficiently roughened textures to permit attachment of the tissue specimen thereto, said support walls being moved apart by said expanding means with said first and second ends and being disposed in substantially perpendicular relation to the direction of separating movement when said first and second ends are separated.

13. In the apparatus of claim 12, said first and second support walls comprising screening elements which substantially define said attachment surfaces thereon, said screening elements being made of a biocompatible material.

14. In the apparatus of claim 13, said screening elements being made of stainless steel.

15. In the apparatus of claim 14, said screening elements having between 4×4 and 250×250 meshes/in, having a wire diameter of between 0.04 mm and 3.76 mm, and a mesh opening width of between 0.06 mm and 2.6 mm.

* * * * *